United States Patent [19]
Hays et al.

[11] Patent Number: 5,972,956
[45] Date of Patent: Oct. 26, 1999

[54] INHIBITION OF AMYLOIDOSIS BY 9-ACRIDINONES

[75] Inventors: Sheryl Jeanne Hays; Harry LeVine, III, both of Ann Arbor; Jeffery David Scholten, Brighton, all of Mich.

[73] Assignee: Warner-Lambert Company, Morris Plains, N.J.

[21] Appl. No.: 09/066,376

[22] PCT Filed: Oct. 18, 1996

[86] PCT No.: PCT/US96/16745

§ 371 Date: Apr. 29, 1998

§ 102(e) Date: Apr. 29, 1998

[87] PCT Pub. No.: WO97/16191

PCT Pub. Date: May 9, 1997

Related U.S. Application Data

[60] Provisional application No. 60/006,388, Nov. 2, 1995.

[51] Int. Cl.⁶ .................................................. A61K 31/47
[52] U.S. Cl. ............................................................. 514/297
[58] Field of Search ............................................. 514/297

[56] References Cited

U.S. PATENT DOCUMENTS 4,626,540 12/1986 Capps ...................................... 514/297

FOREIGN PATENT DOCUMENTS 0 502 668  9/1992  European Pat. Off. .

OTHER PUBLICATIONS

Blanz, Jr., et al., *A Systematic Investigation of Thioxanthen–9–ones and Analogs as Potential Antitumor Agents,* Cancer Inst. vol. 6 (Mar. 1963) pp. 185–191.

Cholody et al., *5–[Aminoalkyl)amino]imidazo[4,5,1–de] acridin–6–ones as a Novel Class of Antineoplastic Agents. Synthesis and Biol. Activity,* J. Med. Chem. (1990) vol. 33, pp. 49–52.

Cholody et al., *Chromophore–Modified Antineoplastic Imidazoacridinones. Synthesis and and Activity against Murine Leukemias,* J. Med. Chem. (1992) vol. 35, pp. 378–382.

*Primary Examiner*—Keith D. MacMillan
*Attorney, Agent, or Firm*—Charles W. Ashbrook

[57] ABSTRACT

Amyloid aggregation in animals is inhibited by administering a 9-acridinone compound of formula I, defined herein. The compounds are especially useful in preventing and treating Alzheimer's disease.

11 Claims, No Drawings

INHIBITION OF AMYLOIDOSIS BY 9-ACRIDINONES

This Application claims priority to Provisional Application No. 60/006,388, filed Nov. 2, 1995.

FIELD OF THE INVENTION

This invention concerns a method for inhibiting amyloidosis utilizing 9-acridinone compounds. The invention is a method for diagnosing and treating diseases characterized by amyloidosis.

BACKGROUND OF THE INVENTION

Amyloid plaque formation is found in a number of diseases, including Alzheimer's disease, scrapie, bovine spongiform encephalophy, Gerstmann-Straussler Syndrome, and the like. The amyloid plaques comprise proteins bound together in a fibrillous matrix. Amyloidosis is the general name given to diseases and conditions characterized by the presence of amyloid protein. A number of different types of amyloid protein are known, and all types are considered pathological, since no normally occurring amyloids are known. Accordingly, the presence of amyloid protein in a host is an indication of abnormal formation of fibrils and plaques. Amyloidosis has been clinically observed in a number of disease states, including certain mental illnesses, neurological diseases, and collagenosis. Indeed, the brains of subjects diagnosed with Alzheimer's disease have one thing in common, namely an abundance of amyloid in the form of plaques and tangles.

Alzheimer's disease is a degenerative brain disorder characterized clinically by progressive loss of memory, cognition, reasoning, judgement, and emotional stability that gradually leads to mental deterioration and ultimately death. To date, only one clinically approved treatment is available, namely tacrine hydrochloride (Cognex®, from the Parke-Davis Division of Warner-Lambert Company). Because Alzheimer's disease and related degenerative brain disorders are a major medical issue for an aging population, the need for new treatments and methods for diagnosing the disorders are needed.

We have now discovered that certain 9-acridinone compounds inhibit amyloid aggregation. The acridinone compounds are described as antibacterial and antitumor agents by Capps in U.S. Pat. No. 4,626,540. The compounds are also described as antitumor agents by Cholody, et al., in *J. Med. Chem.*, 1990;33:49–52 and 1992;35:378–382. These references are incorporated herein by reference for their teaching of synthesis.

SUMMARY OF THE INVENTION

This invention provides a method for inhibiting amyloid aggregation in a mammal by administering a 9-acridinone compound. More particularly, the invention is a method for preventing amyloidosis comprising administering to a mammal an effective amount of a compound having the formula

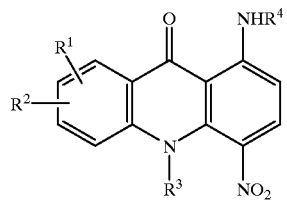

wherein:

$R^1$ and $R^2$ independently are hydrogen, halo, nitro, amino, hydroxy, trifluoromethyl, $C_1$–$C_4$ alkyl-(O or S)$_{0\ or\ 1}$, or $R^5R^6$N-alkylene-(O or S)$_{0\ or\ 1}$;

$R^3$ is hydrogen or $C_1$–$C_4$ alkyl;

$R^4$ is -alkylene-$NR^5R^6$;

alkylene is a $C_2$–$C_4$ straight or branched hydrocarbon chain;

$R^5$ and $R^6$ independently are hydrogen, $C_1$–$C_4$ alkyl, hydroxy $C_1$–$C_4$ alkyl, or taken together with the nitrogen to which they are attached are piperidyl or pyrrolidinyl, and the pharmaceutically acceptable salts thereof.

A preferred method for inhibiting amyloid aggregation employs a compound of the above formula wherein $R^1$ and $R^2$ independently are hydrogen, hydroxy, $C_1$–$C_4$ alkyl—O—, or $C_1$–$C_4$ alkyl—S—.

Another preferred embodiment employs a compound of the above formula wherein $R^4$ is —$(CH_2)_n$—$NR^5R^6$;

$R^5$ and $R^6$ both are methyl or ethyl; and n is 2 or 3.

The most preferred method of the invention employs compounds of the above formula wherein $R^3$ is hydrogen.

DETAILED DESCRIPTION OF THE INVENTION

In the above formula, $R^1$ and $R^2$ can be "$C_1$–$C_4$ alkyl (O or S)$_{0\ or\ 1}$". This term means a straight or branched alkyl group of up to 4 carbons, optionally bonded through oxygen or sulfur. Typical groups include methyl, methoxy, methylthio, ethoxy, ethylthio, isopropyl, isopropoxy, tert.-butoxy, and the like. $R^1$ and $R^2$ can additionally be "$R^5R^6$N-alkylene-(O or S)$_{0\ or\ 1}$." This term means a $C_2$–$C_4$ straight or branched alkylene group having attached to it an amino, substituted amino, or disubstituted amino group, and optionally bonded through an oxygen or sulfur atom. Examples include 2-aminoethyl, 3-aminopropoxy, 2-amino-1-methylpropylthio, 2-methylaminoethyl, 2-N,N-diethylaminoethoxy, 3-piperidinopropyl, 4-pyrrolidinobutylthio, and the like.

$R^4$ is a $C_2$–$C_4$ alkylene group having attached to it a terminal amino, substituted or disubstituted amino group ($NR^5R^6$). The amino substituents can be $C_1$–$C_4$ alkyl or a $C_1$–$C_4$ alkyl having a hydroxy group attached as a substituent. Typical hydroxy —$C_1$–$C_4$ alkyl groups include hydroxymethyl, 3-hydroxypropyl, 4-hydroxybutyl, and the like. Examples of $R^4$ alkylene-$NR^5R^6$ groups therefore are 2-aminoethyl, 3-aminopropyl, 3-N-ethylaminopropyl, 3-(N-ethyl-N-hydroxymethyl)propyl, 3-pyrrolidinopropyl, and the like.

The compounds to be utilized in the method of this invention are known. The compounds preferably are employed as acid addition salts, thereby facilitating oral absorption and solubility. The pharmaceutically acceptable salts are prepared in normal fashion by reacting an amine of the above formula with an organic or inorganic acid such as citric acid, oxalic acid, hydrochloric acid, and the like.

The ability of the 9-acridinone compounds of the above formula to inhibit amyloid aggregation has been established in a standard in vitro assay. The assay is carried out by mixing beta amyloid peptide (1–40) with radioiodinated ($I^{125}$) labeled peptide to a concentration of 2.5 mg/mL in hexafluoroisopropanol. The mixture is diluted 1 to 5 with water (v/v). Ten milliliters of the solution is mixed with 25 μL of 25 mM sodium phosphate buffer pH 6.0. The mixture is allowed to aggregate for 2 hours at room temperature with and without a test compound present. The mixtures are then diluted to 235 μL with phosphate buffer to stop the aggregation process. The solutions are passed through a 0.2-μm millipore filtermat. Aggregated protein remains in the filter well. The filter plate is washed with 50 μL of phosphate buffer and then soaked in solid gel scintillant and counted on a Microbeta counter to determine the amount of aggregation in the presence of a test compound versus control with no test compound.

Several representative 9-acridinone compounds have been evaluated in the above assay and shown to inhibit amyloid aggregation. The following table presents the activity of selected compounds, reported as the molar concentration of compounds required to cause a 50% inhibition ($IC_{50}$) of amyloid aggregation in the above assay.

TABLE I

| Compound No. | $R^1$ | $R^2$ | n | $R^5$ | $R^6$ | $IC_{50}$ (μM) |
|---|---|---|---|---|---|---|
| 1 | 7-SMe | H | 3 | Me | Me | 7.1 |
| 2 | 7-SMe | H | 2 | Et | Et | 9.0 |
| 3 | 6-OMe | 7-OMe | 2 | Et | Et | 11.0 |
| 4 | 7-OBu | H | 2 | Me | Me | 25.0 |
| 5 | 7-OMe | H | 3 | Et | Et | 21.0 |
| 6 | 7-OMe | 6-Cl | 2 | Et | Et | 18.7 |
| 7 | 7-O(CH$_2$)$_2$NEt$_2$ | H | 2 | Et | Et | 35.6 |
| 8 | 7-OEt | H | 2 | —(CH$_2$)$_2$OH | —(CH$_2$)$_2$OH | 20.0 |
| 9 | 7-OH | H | 2 | Et | Et | 20.5 |
| 10 | 7-OMe | H | 2 | Et | Et | 13.9 |
| 11 | H | H | 2 | Et | Et | 29.5 |
| 12 | 7-OMe | H | 2 | Et | Et | 23.2 |
| 13 | 7-OEt | H | 4 | Me | Me | 24.3 |

The compounds of Formula I also have been evaluated utilizing human brain tissue. In a typical experiment, 30 μmol of compound (e.g., Compound No. 9) was mixed with 20 μmol of $I^{125}$-radiolabelled β-amyloid peptide (1–40) in a solution of 50 mmol of Tris (ph=7.4) containing 4% (v/v) of bovine serum albumin to reduce nonspecific binding. The solution was stored at 25° C. for 1 hour. Thin sections (about 20 μmeters) of human cadaver brain tissue were affixed to glass slides, and the slides were placed in the amyloid solution for 6 hours at 25° C. The glass slides were withdrawn, rinsed with cold (10° C.) phosphate-buffered saline (PBS), fixed in 5% glutaraldehyde, and finally rinsed again sequentially with PBS and dehydrated ethanol. The slides were X-rayed using a Phosphorimager cassette (Molecular Dynamics) and dipped in photographic emulsion.

The brain tissues exposed to Compound No. 9 had 20% to 30% less radioactive grain accumulations when compared to untreated brain tissue. The grain accumulations are associated with amyloid plaques. The data thus demonstrates the test compound decreases the number and size of amyloid plaques. No grain accumulations appeared in human cerebellar sections, or associated with blood vessels.

For inhibition of amyloid aggregation according to this invention, all that is required is to administer to a mammal an effective amount of a 9-acridinone compound as defined above. An "effective amount" as used herein is that quantity of 9-acridinone compound which inhibits aggregation of amyloid protein without causing unacceptable toxic effects. Typical doses which are effective will be from about 0.1 to about 1000 mg/day, and more typically from about 50 to about 500 mg/day. The compounds can be administered from one to about three times a day for either prophylactic or therapeutic treatment of diseases related to the deposition of one or more amyloidogenic proteins, for example Alzheimer's disease, Down's syndrome, and in general advanced aging of the brain.

The 9-acridinone compounds can be formulated for convenient administration orally or parenterally, for instance by intravenous or intramuscular routes. The compounds also are well suited to transdermal delivery, and can thus be formulated as patches, creams, lotions, and the like. Typical formulations for oral administration will be made by mixing the 9-acridinone compound with common diluents and excipients such as corn starch, sugar, talc, and the like, and forming tablets, capsules, caplets, syrups, suspensions, and the like. For parenteral delivery, the compounds are ideally dissolved in isotonic saline or aqueous glucose for injection or intravenous delivery. The compounds can also be formulated with waxes and polymers and molded into suppositories or other common sustained-release delivery forms. The 9-acridinone compounds are preferably converted to pharmaceutically acceptable salts to increase solubility and facilitate formulation and administration.

Because the 9-acridinone compounds described above are also effective at binding to amyloids, they can additionally be utilized to detect amyloid deposition, and thus to detect disease states associated with amyloid aggregation, such as Alzheimer's disease.

The compounds can readily be radiolabeled with common radioisotopes such as $I^{125}$, $C^{11}$, tritium, or the like. For example, compounds wherein $R^1$ or $R^2$ are halo can be made with $I^{125}$. Any of the carbons present in the compounds can be $C^{11}$. The radiolabeled compounds are synthesized as described in the references cited above, and employing common synthetic techniques utilizing readily available radioactive chemicals. The radiolabeled compound is then formulated and administered to a mammal in the same manner as described above for nonradiolabeled compounds. The mammal can then be scanned with common imaging sensors and equipment to detect amyloid deposition and aggregation.

We claim:

1. A method for inhibiting amyloid aggregation in a mammal comprising administering an effective amount of a compound having the formula

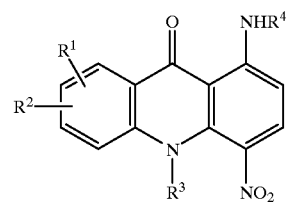

wherein:

$R^1$ and $R^2$ independently are hydrogen, halo, nitro, amino, hydroxy, trifluoromethyl, $C_1$–$C_4$ alkyl-(O or S)$_{0\ or\ 1}$, or $R^5R^6$N-alkylene-(O or S)$_{0\ or\ 1}$;

$R^3$ is hydrogen or $C_1$–$C_4$ alkyl;

$R^4$ is -alkylene-$NR^5R^6$;

alkylene is a $C_2$–$C_4$ straight or branched hydrocarbon chain;

$R^5$ and $R^6$ independently are hydrogen, $C_1$–$C_4$ alkyl, hydroxy-$C_1$–$C_4$ alkyl, or taken together with the nitrogen to which they are attached are piperidyl or pyrrolidinyl, and the pharmaceutically acceptable salts thereof.

2. A method according to claim 1 employing a compound having the formula

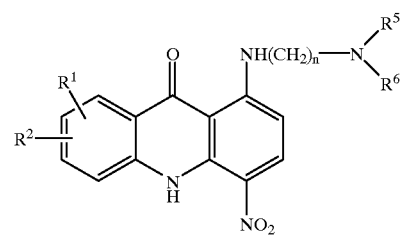

wherein:

$R^1$ and $R^2$ independently are hydrogen, hydroxy, $C_1$–$C_4$ alkyl—O—, or $C_1$–$C_4$ alkyl—S—;

$R^5$ and $R^6$ both are methyl or ethyl;

and n is 2 or 3.

3. A method according to claim 2 employing a compound wherein n is 2 and $R^5$ and $R^6$ both are ethyl.

4. A method according to claim 3 employing a compound wherein $R^1$ is hydrogen, 7-methylthio, 7-methoxy or 7-hydroxy, and $R^2$ is hydrogen, 6-chloro, or 6-methoxy.

5. A method according to claim 2 employing a compound wherein n is 3 and $R^5$ and $R^6$ both are methyl or ethyl.

6. A method according to claim 5 employing a compound wherein $R^1$ is 7-methoxy or 7-methylthio, and $R^2$ is hydrogen.

7. A method according to claim 1 employing a compound having the formula

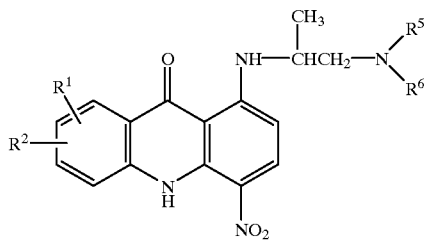

wherein:

R$^1$ and R$^2$ independently are hydrogen, hydroxy, C$_1$–C$_4$ alkyl—O—, or C$_1$–C$_4$ alkyl—S—; and R$^5$ and R$^6$ both are methyl or ethyl.

8. A method according to claim 7 employing a compound wherein R$^1$ is 7-ethoxy, and R$^2$ is hydrogen.

9. A method according to claim 1 employing a compound wherein R$^3$ is C$_1$–C$_4$ alkyl.

10. A method according to claim 9 employing a compound wherein R$^3$ is methyl.

11. A method of diagnosing a mammal having amyloid aggregation comprising administering an effective amount of a radiolabeled compound of the formula

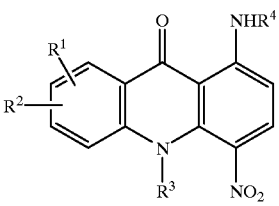

wherein:

R$^1$ and R$^2$ independently are hydrogen, halo, nitro, amino, hydroxy, trifluoromethyl, C$_1$–C$_4$ alkyl-(O or S)$_{0 \text{ or } 1}$, or R$^5$R$^6$N-alkylene-(O or S)$_{0 \text{ or } 1}$;

R$^3$ is hydrogen or C$_1$–C$_4$ alkyl;

R$^4$ is -alkylene-NR$^5$R$^6$;

alkylene is a C$_2$–C$_4$ straight or branched hydrocarbon chain;

R$^5$ and R$^6$ independently are hydrogen, C$_1$–C$_4$ alkyl, or taken together with the nitrogen to which they are attached are piperidyl or pyrrolidinyl, and the pharmaceutically acceptable salts thereof;

and wherein at least 1 atom is radioactive, and imaging the mammal to determine the accumulation of the compound in brain tissue.

* * * * *